United States Patent
Hanke

(10) Patent No.: US 7,713,189 B2
(45) Date of Patent: May 11, 2010

(54) VIDEO ENDOSCOPE WITH A ROTATABLE VIDEO CAMERA

(75) Inventor: Harald Hanke, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 1095 days.

(21) Appl. No.: 11/220,809

(22) Filed: Sep. 7, 2005

(65) Prior Publication Data

US 2006/0058581 A1    Mar. 16, 2006

(30) Foreign Application Priority Data

Sep. 11, 2004    (DE) .................. 10 2004 044 119

(51) Int. Cl.
*A61B 1/04* (2006.01)

(52) U.S. Cl. ............... 600/109; 600/129; 600/130; 600/137

(58) Field of Classification Search ............. 600/101, 600/102, 109, 112, 129, 130, 134, 137, 173
See application file for complete search history.

(56) References Cited

U.S. PATENT DOCUMENTS

| | | | |
|---|---|---|---|
| 4,600,940 A | | 7/1986 | Sluyter |
| 5,156,141 A * | | 10/1992 | Krebs et al. ............. 600/112 |
| 5,662,588 A * | | 9/1997 | Iida ........................ 600/121 |
| 5,797,836 A * | | 8/1998 | Lucey et al. ............. 600/109 |
| 6,371,907 B1* | | 4/2002 | Hasegawa et al. ........ 600/146 |
| 6,450,550 B1* | | 9/2002 | Cornwell ................ 285/340 |
| 6,464,631 B1* | | 10/2002 | Girke et al. ............. 600/109 |
| 6,522,477 B2* | | 2/2003 | Anhalt ................... 359/694 |
| 2002/0051642 A1* | | 5/2002 | Hicks .................... 396/429 |
| 2002/0128538 A1* | | 9/2002 | Thompson ............... 600/121 |
| 2005/0275725 A1* | | 12/2005 | Olsson et al. ........ 348/207.99 |

FOREIGN PATENT DOCUMENTS

DE    201 13 031 U1    1/2002

* cited by examiner

*Primary Examiner*—John P Leubecker
*Assistant Examiner*—Samuel Candler
(74) *Attorney, Agent, or Firm*—Rankin, Hill & Clark LLP

(57) ABSTRACT

A video endoscope includes a tube fitted at its distal end with an affixed objective lens, a video camera mounted behind the objective lens in the tube, the camera together with an elongated rotation element constituting a swivel unit that is supported both at the distal and proximal end zones in each case by swivel bearing at the tube. The swivel element being rotationally adjustable relative the tube by a swivel drive system. The distal swivel bearing is axially and radially bearing and the proximal swivel bearing is only radially bearing.

3 Claims, 2 Drawing Sheets

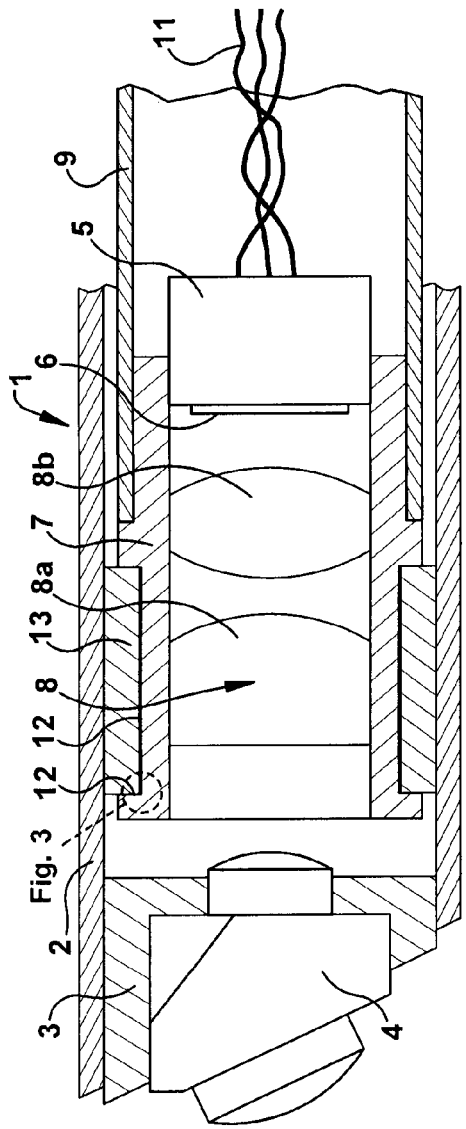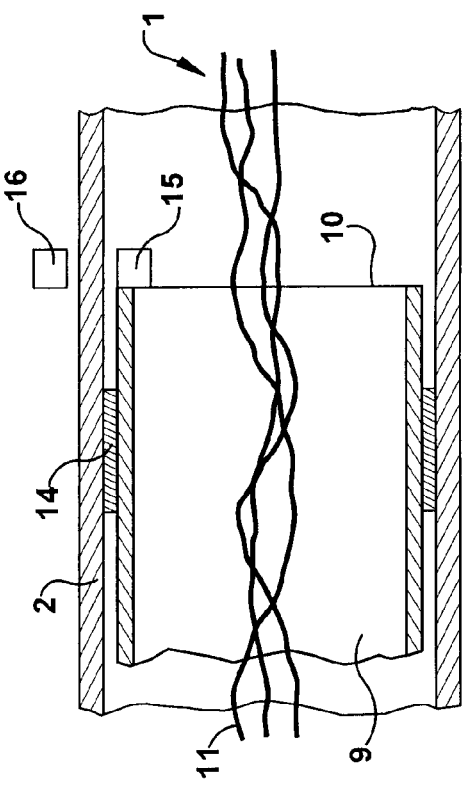
Fig. 1
Fig. 2

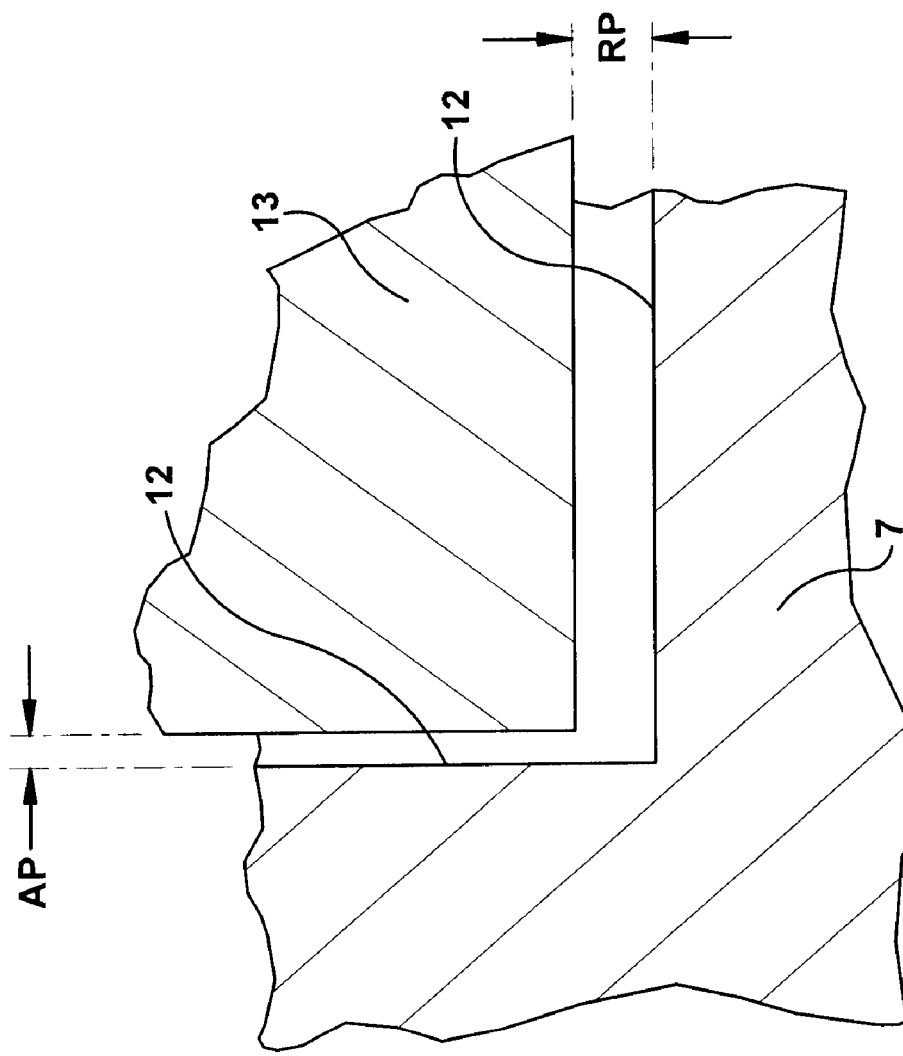

VIDEO ENDOSCOPE WITH A ROTATABLE VIDEO CAMERA

BACKGROUND OF THE INVENTION

1. Field of the Invention

The present invention generally relates to a video endoscope and, more particularly, toward an endoscope with a rotatable video camera.

2. Description of Related Art

When used in procedures in the human body, endoscopes frequently need to be rotated or swiveled so that an implement fitted into the endoscope may reach a particular place or, for instance, to be able to observe laterally when the objective lens is oblique. When the video camera however is irrotationally mounted in the video endoscope, the monitor picture shall rotate jointly with the video endoscope. This feature is highly taxing for the surgeon.

Accordingly video endoscopes of this kind are fitted with a rotatable camera which can be rotated relative to the video endoscope rotation such that the monitor picture shall remain unaffected by camera rotation.

The German patent document U 20,113,031 discloses a video endoscope wherein, on well known design grounds coming into play in particular with oblique objective lenses, the objective lens is affixed to the tube enclosing the swivel unit, and the tube is fixed in position relative to the endoscope as a whole. Accordingly, in this design the video camera rotates relative to the objective lens. The rotational system of video camera and rotational element is supported on two swivel bearings to assure accurate guidance and bracing of the video camera relative to the objective lens. Moreover, an axially fixed bearing ensures the axial position between camera and objective lens.

This known design incurs the drawback that the axial bearing is situated at the proximal end of the swivel element. If the endoscope is being bent and when there are temperature changes such as frequently occur when using video endoscopes (body temperature/room temperature), the distance between objective lens and video camera may change and degrade the focus, i.e., they may entail a blurred picture.

SUMMARY OF THE INVENTION

The present invention is directed toward improving focusing in the above kind of video endoscopes.

In the present invention, the distal swivel bearing is designed for axial bearing. In this manner, the video camera is always reliably at the precise focusing distance from the objective lens, whereas the proximal end of the rotational element is allowed to easily move axially on account of being bent or undergoing temperature changes. In this manner, good focus is assured under all possible conditions.

In further accordance with the present invention, the distal swivel bearing is a simple slide bearing. The required space, in particular in the radial direction, is small, and as a result a large-area and hence highly resolving video camera may be used even when the outside diameter of the video endoscope is small. By using a ceramic slide ring, the tube and the camera are electrically insulated, keeping the patient safe from electrical shock or exposure.

If the ceramic ring were to fit precisely into the external groove, jamming might occur, for instance, if the temperatures were to change. Accordingly, the present invention advantageously provides some play in both guide directions. A few hundredths of a mm are adequate for this purpose and do not significantly hamper optical alignment and focusing.

This design offers the significant advantage that no stresses are exerted on the ceramic ring in the external groove and, accordingly, the ring swivels very freely. Therefore the video camera allows fine manual control and is free from jerky motion.

If the entire objective lens were fixed, every play of the video camera relative to the tube would interfere with the proper imaging on said camera. Accordingly, in the present invention a proximal portion of the objective lens is affixed to the camera to be swiveling jointly with it and, consequently, to be lined up entirely free of play relative to the camera. The two portions of the objective lens may be designed such that a substantially collimated beam, which is insensitive to radial and axial shifts, shall be set up between them. In this way the imaging quality is substantially increased regardless of deviations due to play and adjustments.

BRIEF DESCRIPTION OF THE INVENTION

These and further features of the invention will be apparent with reference to the following description and drawings, wherein:

FIG. 1 is an axial section of the distal end zone of a video endoscope of the present invention, and FIG. 2 shows, in the same axial section, a proximal zone of the video endoscope.

FIG. 3 shows a detailed view of a portion of FIG. 1 showing axial play "AP" and radial play "RP".

DETAILED DESCRIPTION OF THE PREFERRED EMBODIMENTS

FIG. 1 shows the distal end zone of the significant portions of a video endoscope 1. An objective lens fixture 3 is affixed in a tube 2 at the far distal end and holds a distally fixed portion 4 of the objective lens. In the shown embodiment, the distal objective lens portion 4 consists of a prism and two lens elements. A video camera 5 with an imaging detector plate 6 is affixed in an annular camera case 7 which, moreover, contains two lens elements 8a and 8b that constitute a proximal portion 8 of the objective lens.

A rotating tube 9 constituting a rotating drive element is affixed to the camera case 7 and runs through the tube 2 as far as the proximal end zone (FIG. 2) where it terminates at 10. Hookup cables 11 of the video camera 5 run through the rotating tube 9.

The camera case 7 is fitted with an external groove 12 by means of which it is guided in sliding manner in a ceramic ring 13 which, in turn, is affixed in the tube 2. The camera case 7 and, jointly with it, the video camera 5 rests in axially fixed manner by means of the external groove 12 on the ceramic ring 13, and therefore cannot move either distally or proximally. This design also radially supports the video camera 5 with respect to the tube 2. There is a given axial play, illustratively at least a few hundredths of a mm, between the external groove and the ceramic ring 13 to minimize friction.

The rotating tube 9 is supported merely radially by a slide ring 14. This design allows mutual axial shifting between the tubes 9 and 10.

The slide ring 14 is made of an insulating material, as is the ceramic ring 13, in order to electrically insulate the tubes 2 and 9 from each other. This feature safeguards the patient against electrical exposure or shock in the event the metallic camera case 7 or the metallic rotating tube 9 should make accidental contact with electrified parts of the video camera 5 or with the hookup cables 11.

The rotating tube 9 is rotatable at its proximal end 10 by means of a rotation drive element. For that purpose, in the shown embodiment a permanent magnet 15 is affixed to the proximal end of the rotating tube 9 and can be rotated using a permanent magnet 16 configured outside the video endoscope, with the latter permanent magnet 16 illustratively being configured on the outside of the video endoscope 1 to a rotation ring (not shown). To implement such a design, the material of the tube 2 must be sufficiently magnetically permeable and may be, for instance, made of a high-grade steel.

The two portions 4 and 8 of the objective lens are designed such that in-between them (i.e., between the proximal end lens element of the distal objective lens portion 4 and the distal end lens element 8a of the proximal objective portion 8), the beam shall be as collimated as possible to preclude relative shifts between the two objective lens portions. Such relative shifts could be caused, for instance, by adjustment errors, plays or other mechanical deviations, which in this design shall not significantly degrade the endoscope imaging properties.

An external tube (not shown) encloses the tube 2 and is hermetically sealed distally by a window in front of the objective lens 4, which, in this instance, is configured obliquely, to protect the objective lens 4, 8 and the camera 5 against otherwise penetrating water vapor. Moreover, in conventional manner, a light guide, for instance in the form of a fiber optics and used for illumination, may be mounted outside the above mentioned external tube, and, together with the shown video endoscope 1, it may once more be received in an outermost enclosing tube.

In the embodiment shown herein, the objective lens 4, 8 using the shown prism, does look obliquely forward. In other embodiments, however, the objective lens 4, 8 may also be designed to be straight forward looking.

The objective lens 4, 8 is shown in the embodiment herein as being in two portions. However, the object lens 4, 8 may also be in one portion and fixed in position, with the proximal objective lens portion 8 being eliminated and the distal objective lens portion 4 being configured in a different lens element array and closer to the video camera 5.

Also, the camera case 7 may be other than shown herein. For instance, the camera case may be integral with the rotating tube 9. In particular with respect to assembly procedures, the camera case may also be disassemblable into components.

The invention claimed is:

1. A video endoscope comprising a tube fitted at its distal end with an affixed distal portion of an objective lens, further comprising a video camera mounted behind the distal objective lens portion in the tube, said camera together with a rotation element constituting a swivel unit having a distal end zone in which the video camera is located and a proximal end zone, said swivel unit distal end zone being supported by a distal swivel bearing close to the video camera and said swivel unit proximal end zone being supported by a proximal swivel bearing, the swivel unit being rotationally adjustable relative the tube by a swivel drive system, wherein the distal swivel bearing limits axial movement of the distal end zone of the swivel unit in both the distal and the proximal directions relative to the tube and wherein the proximal swivel bearing permits axial movement of the proximal end zone of the swivel unit in both the distal and the proximal directions relative to the tube, wherein the distal swivel bearing comprises a ceramic ring that is affixed to the tube and runs in an external groove of a camera case to which are affixed both the video camera and the rotation element.

2. The video endoscope as claimed in claim 1, wherein both a radial play and an axial play are present between the ceramic ring and the external groove.

3. The video endoscope as claimed in claim 1, wherein a proximal portion of the objective lens is affixed to the swivel unit, and wherein the distal portion of the objective lens and the proximal portion of the objective lens are arranged such that an at least approximately collimated light beam is set up between them.

\* \* \* \* \*